(12) United States Patent
Fuugetsu

(10) Patent No.: US 7,691,358 B2
(45) Date of Patent: Apr. 6, 2010

(54) NANOCARBON SOLUBILIZER, METHOD FOR PURIFYING SAME, AND METHOD FOR PRODUCING HIGH-PURITY NANOCARBON

(75) Inventor: Bunshi Fuugetsu, Sapporo (JP)

(73) Assignee: National University Corporation Hokkaido University, Sapporo-shi, Hokkaido (JP)

(*) Notice: Subject to any disclaimer, the term of this patent is extended or adjusted under 35 U.S.C. 154(b) by 944 days.

(21) Appl. No.: 10/537,478

(22) PCT Filed: Dec. 2, 2003

(86) PCT No.: PCT/JP03/15445

§ 371 (c)(1),
(2), (4) Date: Jun. 3, 2005

(87) PCT Pub. No.: WO2004/060798

PCT Pub. Date: Jul. 22, 2004

(65) Prior Publication Data

US 2005/0277675 A1    Dec. 15, 2005

(30) Foreign Application Priority Data

Dec. 6, 2002    (WO) .................. PCT/JP02/12815

(51) Int. Cl.
  *C01B 31/02*    (2006.01)
(52) U.S. Cl. ............... 423/445 B; 423/461; 423/447.1; 977/734; 977/738; 977/742; 977/746; 977/906
(58) Field of Classification Search ........... 423/461, 423/447.1, 447.2, 447.3, 460, 445 B; 977/830, 977/734, 738, 742, 746, 906
See application file for complete search history.

(56) References Cited

U.S. PATENT DOCUMENTS

| | | | | |
|---|---|---|---|---|
| 5,641,466 | A * | 6/1997 | Ebbesen et al. | ........... 423/447.2 |
| 6,015,686 | A * | 1/2000 | Dubensky et al. | ........... 435/69.1 |
| 6,331,262 | B1 * | 12/2001 | Haddon et al. | ............... 252/502 |
| 6,683,783 | B1 * | 1/2004 | Smalley et al. | ............... 361/502 |
| 2005/0152891 | A1 * | 7/2005 | Toone et al. | ............... 424/125 |

FOREIGN PATENT DOCUMENTS

| | | |
|---|---|---|
| JP | 06-228824 B2 | 8/1994 |
| JP | 8-198611 A | 8/1996 |
| JP | 2001-48511 A | 2/2001 |

OTHER PUBLICATIONS

Bandyopadhyaya, et al., Stabilization of Individual Carbon Nanotubes in Aqueous Solutions, Nano Letters 2002; 2(1): 25-28.*
Dullavet, et al., Meaning of molecular weight gum arabic measurements, Polymer Bulletin 1989; 21: 517-521.*
Nakashima, et al, DNA Dissolves Single-walled Carbon Nanotubes in Water, Chemistry Letters 2003: 32(5): 456-457.*
Okuzono, DNA Kayoka Carbon Nanotube Kozo to Tokushei, Polymer Preprints, Japan Yokoshu 2003; 52(13): 3732-3733.*
U.S. Appl. No. 60/377,862 to Toone, et al. (filed May 3, 2002).*
English translation of International Preliminary Examination Report in International Application No. PCT/JP2003/015445 (Forms PCT/IB/338 (1 page) and PCT/IPEA/409 (4 pages).
J-M. Bonard et al., "Purification and Size-Selection of Carbon Nanotubes," *Advanced Materials*, 1997, vol. 9, No. 10, pp. 827 to 831.
G.S. Duesberg et al., "Chromatography of Carbon Nanotubes," *Synthetic Metals*, 1999, vol. 103, pp. 2484 to 2485.
N. Nakashima et al., "DNA Dissolves Single-walled Carbon Nanotubes in Water," *Chemistry Letters*, May 5, 2003, vol. 32, No. 5, pp. 456 to 457.
Shingo Okuzono et al., "DNA Kayoka Cabon Nanotube Kozo to Tokushei," *Polymer Preprints*, Japan Yokoshu, Sep. 10, 2003, vol. 52, No. 13, pp. 3732 to 3733.
Shingo Okuzono et al., "DNA Kayoka Cabon Nanotube Kozo to Tokushei," *Polymer Preprints*, Japan Yokoshu, Sep. 10, 2003, vol. 52, No. 13, pp. 3732 to 3733 (English Language Abstract Enclosed).
Shingo Okuzono et al., "DNA Kayoka Cabon Nanotube Kozo to Tokushei," *Polymer Preprints*, Japan Yokoshu, Sep. 10, 2003, vol. 52, No. 13, pp. 3732 to 3733 (English Language Abstract Also Enclosed).

* cited by examiner

Primary Examiner—Stanley S. Silverman
Assistant Examiner—Daniel C. McCracken
(74) Attorney, Agent, or Firm—Frishauf, Holtz, Goodman & Chick, P.C.

(57) ABSTRACT

A water solubilizer for nanocarbons contains a surfactant which can form a spherical micelle vesicle having a diameter of 50-2,000 nm in a water solution or a water-soluble polymer having a weight-average molecular weight of 10,000-50,000,000 as an active constituent. For example, the water solubilizer is used for purification of nanocarbons.

6 Claims, 4 Drawing Sheets

Figure 1:
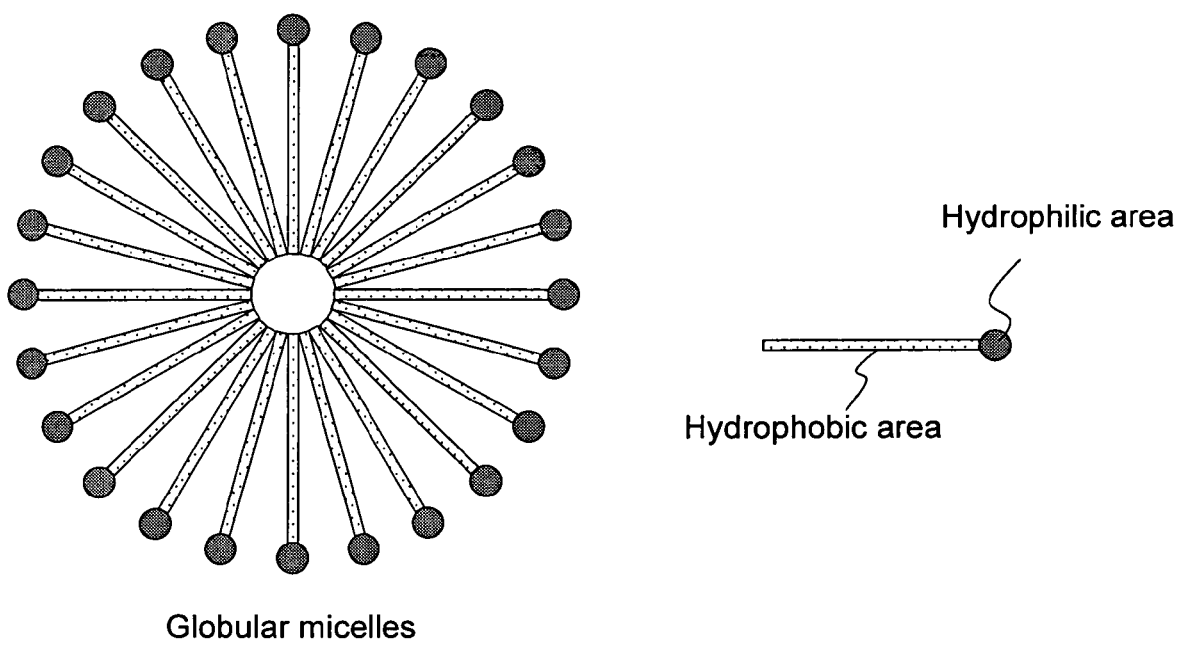
Figure 2:
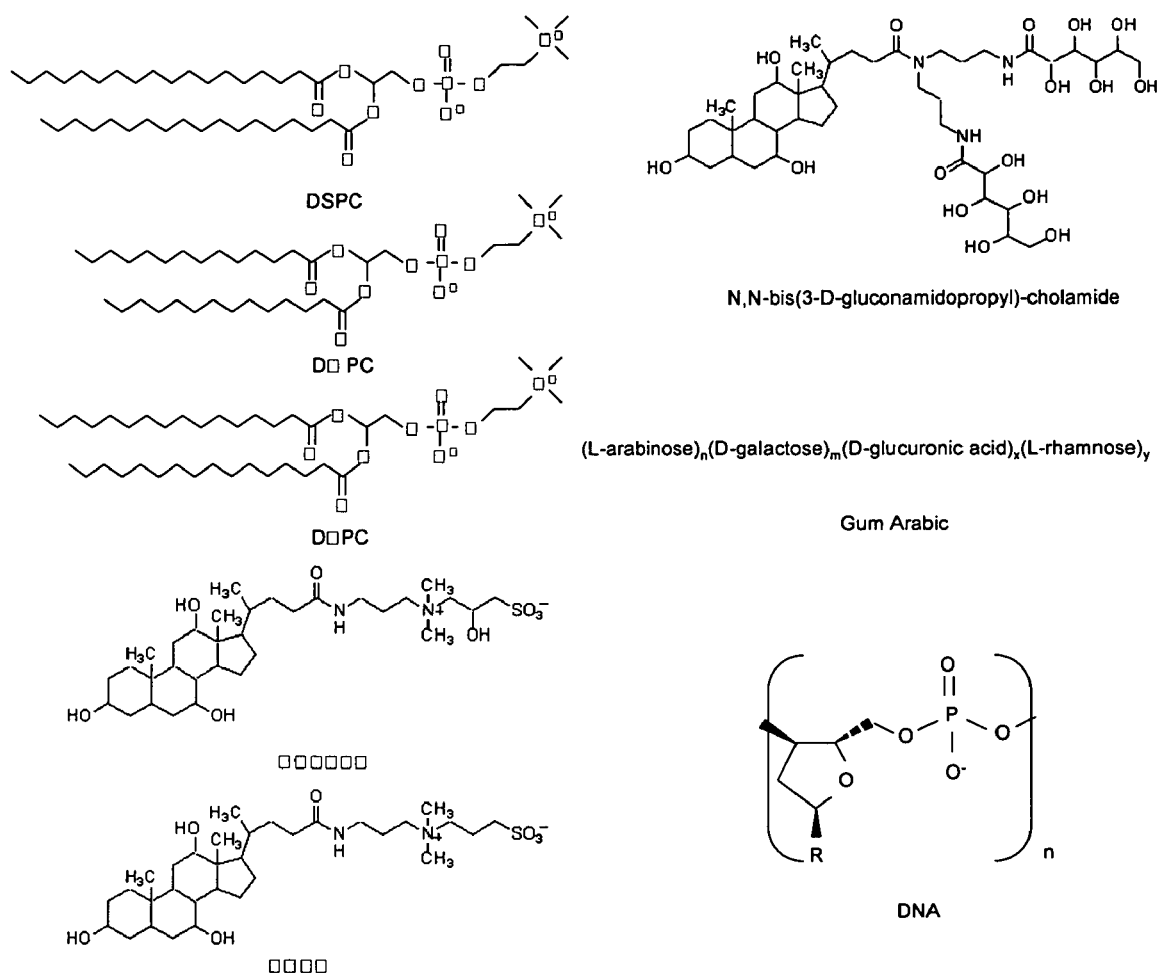
Figure 3:
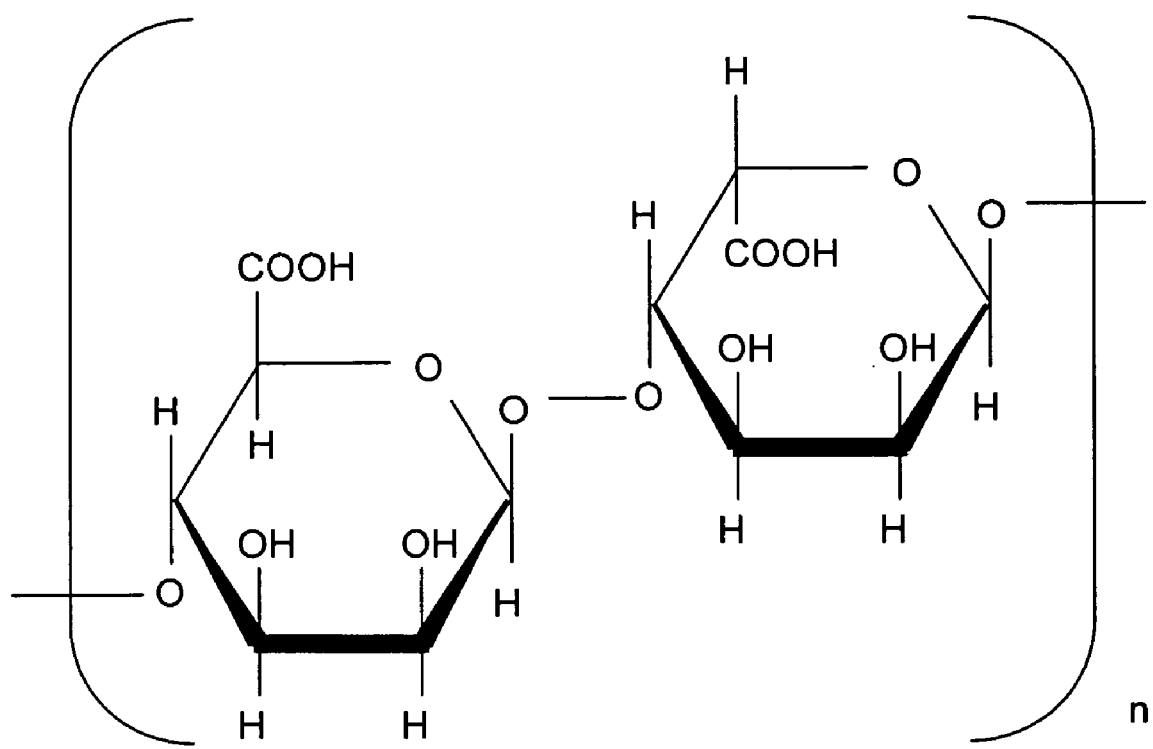
Figure 4:
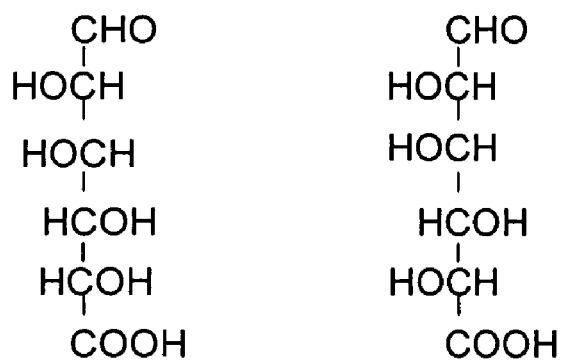
Figure 4:
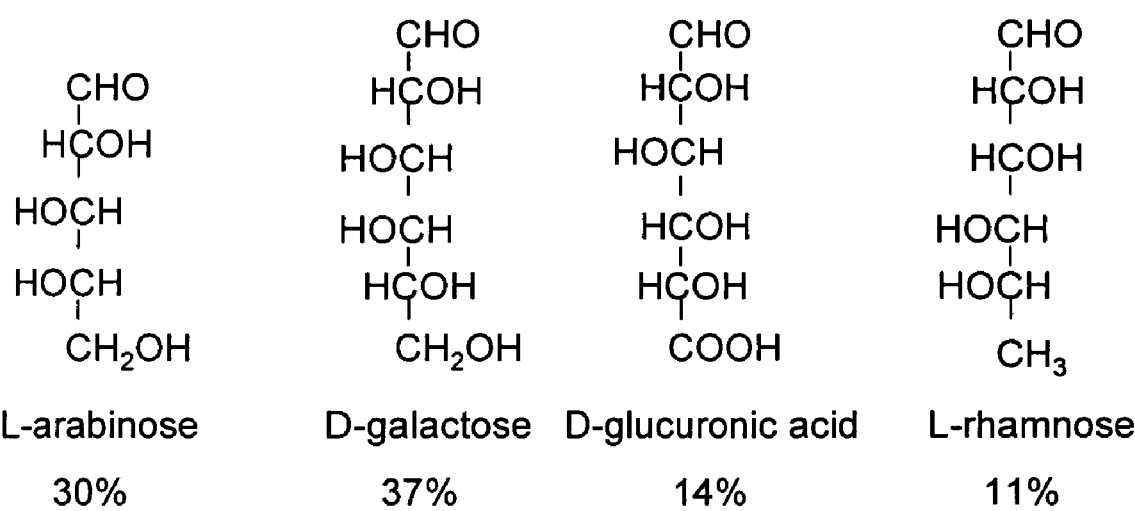

NANOCARBON SOLUBILIZER, METHOD FOR PURIFYING SAME, AND METHOD FOR PRODUCING HIGH-PURITY NANOCARBON

This application is a U.S. National Phase Application under 35 USC 371 of International Application PCT/JP03/15445, filed Dec. 2, 2003, which is incorporated herein in its entirety by this reference.

TECHNICAL FIELD

The present invention relates to the art of easily obtaining high-purity nanocarbons from crude nanocarbon products, in particular, a nanocarbon solubilizing agent (solubilizer) (for example, a form of an aqueous solution capable of solubilizing carbon nanotubes), a process for refining (purifying) nanocarbons using the same and a process for producing high-purity nanocarbons.

BACKGROUND ART

Nanocarbon is a new material, represented by carbon nanotube, which draws attentions in various fields of energy, electronics, chemistry, pharmaceuticals, optics, materials and mechanics, etc. Carbon nanotubes include single- and multi-layered types and cup-stack types. The single- and multi-layered types are needle-like carbon molecules having a diameter in the order of nanometers and have a structure of graphene rolled into a cylinder. Those having a multi-layer structure composed of concentrically placed graphene cylinders are called multi-walled carbon nanotubes, while those consisting of a single layer of graphene cylinder are called single-walled carbon nanotubes.

Incidentally, there have conventionally been a number of procedures provided for refining crude carbon nanotube products. For example, Japanese Unexamined Patent Publication (Kokai) No. 2000-290008 discloses a process for refining carbon tubes which comprises the first step of dispersing a crude product containing carbon tubes into a gold colloidal solution, the second step of removing a solvent from the gold colloidal solution containing the crude product and the third step of heating the crude product under oxygen atmosphere. This technique utilizes the principle that gold tends to act as a catalyst when rendered particulate and oxidize carbon at a low temperature.

In the technique as described in Japanese Unexamined Patent Publication No. 2000-290008, an example of solvents for the solution to be used is water; however, the carbon nanotubes per se exist as dispersed in an aqueous solution without being dissolved.

In addition, the Preliminary Proceedings of 51st Symposium on Macromolecules, Oct. 2 to 4, 2002 at Kyushu Institute of Technology, Kitakyushu, Japan discloses a technique of solubilizing single-layered carbon nanotubes into water. This technique, however, solubilizes carbon nanotubes into water by surface-treating the carbon nanotubes with an amphipathic compound having a bilene group to impart hydrophilicity to their surfaces. Thus, when the surfaces are modified, such modifications must be removed afterward depending on the application, which makes it quite cumbersome.

The present invention aims to provide a novel technique for solubilizing nanocarbons into water without modifying nanocarbon surfaces.

DISCLOSURE OF THE INVENTION

As a result of trial and error, the inventor has discovered that nanocarbons may be solubilized by encapsulating the nanocarbons in globular micelles (microsomes) or pseudomicelles and has attained the present invention. The term "pseudomicelle" as used herein refers to the state formed by nanocarbons being wrapped around (for example, entwined or enclosed) by a macromolecular surface active agent, in which a substance wrapped around will as a whole exhibit hydrophilicity so that it may be solubilized in a manner similar to the case with micelles.

Specifically, the present invention (1) is a water-solubilizing agent for nanocarbons comprising, as an active ingredient, a surface active agent capable of forming globular micelles having a diameter of from 50 to 2000 nm in an aqueous solution (hereinafter referred to as "micelle type") or a water-soluble macromolecule having a weight average molecular weight of from 10,000 to 50,000,000 (hereinafter referred to as "pseudomicelle type").

The present invention (2) is the water-solubilizing agent according to the invention (1) wherein the surface active agent is a phospholipid- or non-phospholipid-based surface active agent.

The present invention (3) is the water-solubilizing agent according to the invention (2) wherein the surface active agent is one or more selected from the group consisting of distearoylphosphatidylcholine (DSPC), dimyristoylphosphatidylcholine (DMPC), dipalmitoylphosphatidylcholine (DPPC), 3-[(3-cholamidopropyl)dimethylamino]-2-hydroxy-1-propanesulfonate (CHAPSO), 3-[(3-cholamidopropyl)dimethylamino]-propanesulfonate (CHAP) and N,N-bis(3-D-gluconamidopropyl)-cholamide.

The present invention (4) is the water-solubilizing agent according to the invention (1) wherein the water-soluble macromolecule is a vegetable-based surface active agent.

The present invention (5) is the water-solubilizing agent according to the invention (1) wherein the water-soluble macromolecule is a compound selected from water-soluble polylysacchride, such as alginates (for example, alginic acid, propylene glycol alginates), gum arabic, xanthan gum, hyaluronic acid, chondroitin sulfate, water-soluble cellulose, such as cellulose acetate, methyl cellulose, hydroxypropyl methyl cellulose, chitosan, chitosan, chitin; water-soluble proteins, such as gelatin, collagen; polyoxythylene-polyoxypropylene block copolymer; and DNA.

The present invention (6) is the water-solubilizing agent according to any one of the inventions (1) to (5) which is in the form of an aqueous solution.

The present invention (7) is the water-solubilizing agent according to the invention (6) wherein the agent further comprises a nanocarbon-permeating substance and an oxidizing agent and the pH ranges from 6 to 14.

The present invention (8) is the water-solubilizing agent according to the invention (7) wherein the nanocarbon-permeating substance is lithium ion.

The present invention (9) is the water-solubilizing agent according to the invention (7) or (8) wherein the oxidizing agent is a persulfate.

The present invention (10) is the water-solubilizing agent according to any one of the inventions (1) to (9) wherein the nanocarbons are carbon nanotubes (single- and multi-layered types and cup-stack types), carbon nanofibers or carbon nanohorns.

The present invention (11) is the water-solubilizing agent according to any one of the inventions (1) to (10) which is used for refining nanocarbons.

The present invention (12) is a process for refining nanocarbons comprising the step of adding a crude product containing nanocarbons to the water-solubilizing agent as defined in any one of the inventions (6) to (11) in the form of an aqueous solution, thereby dissolving the nanocarbons into the water-solubilizing agent.

The present invention (13) is the process for refining nanocarbons according to the invention (12) which further comprises the step of treating the crude product containing nanocarbons with an acid before adding the crude product to the water-solubilizing agent when a metal catalyst was used in a process for producing the crude product.

The present invention (14) is a process for producing high-purity nanocarbons comprising the step of adding a crude product containing nanocarbons to the water-solubilizing agent as defined in any one of the inventions (6) to (11) in the form of an aqueous solution, thereby dissolving the nanocarbons into the water-solubilizing agent.

The present invention (15) is the process for producing high-purity nanocarbons according to the invention (14) which further comprises the step of treating the crude product containing nanocarbons with an acid before adding the crude product to the water-solubilizing agent when a metal catalyst was used in a process for producing the crude product.

BEST MODE FOR CARRYING OUT THE INVENTION

First of all, water-solubilizing agents on the basis of the micelle type will be described. Surface active agents to be used for this type are those capable of forming globular micelles having a diameter of from 50 to 2000 nm (preferably from 50 to 300 nm) in an aqueous solution. Reasons for the suitability of globular micelles (microsomes) of these sizes are not clear; however, the following assumptions can be made at the moment. For example, carbon nanotubes usually have a length in the range of from 100 to 1000 nm. When a water-solubilizing agent according to the present invention is used in the form of an aqueous solution, the carbon nanotubes will be folded to a fraction of their length (for example, to the order of one-fourth of their length) so that they may have a length of from several tens of nanometers to several hundreds of nanometers in the aqueous solution. It is presumably understood that the above sizes are appropriate for housing such folded carbon nanotubes in the microsomes, with a result that the carbon nanotubes can effectively be solubilized. It is also assumed for other nanocarbons that they may be housed in micelles according to the same mode of action.

There has previously been a technique in which a surface active agent is added (Japanese Unexamined Patent Publication No. 2002-255528). The micelles formed by this technique, however, are very small in the order of 0.1 nm and the principle of the technique is such that carbon nanotubes will adhere to the surfaces of the micelles. The present invention is based upon the new concept that nanocarbons (for example, nanotubes) are housed within micelles (microsomes) instead of adhering to the surfaces of the micelles.

The term "globular micelle" ("microsome") as used herein refers to a micelle formed by a surface active agent, which has a globular housing space. For example, in the case of phospholipid-based surface active agents, such microsomes are called liposomes. The diameter of the globular micelle (microsome) represents a value as determined according to light scattering method (pH-unadjusted aqueous solution at 20° C.).

Surface active agents which may be used are not particularly limited as long as they have the above-specified characteristics. For example, both phospholipid-based surface active agents and non-phospholipid-based surface active agents to be subsequently referred to may be used.

The term "phospholipid-based surface active agent" here means anionic and twitterionic surface active agents having a phosphate group as a functional group, which may be of either a phospholipid (including both glycerophospholipid and sphingophospholipid) or a modified phospholipid (for example, hydrogenated phospholipid, lysophospholipid, enzyme-converted phospholipid, lysophosphatidylglycerol, complexes with other substances). Such phospholipids are found in various membrane systems of organism-composing cells, such as protoplasmic membranes, nuclear membranes, microsome membranes, mitochondrial membranes, Golgi cell membranes, lysosomal membranes, chloroplast envelopes and bacterial cell membranes. Preferably, phospholipids used for liposome preparation are preferable. Specific examples may include phosphatidylcholines [such as distearoylphosphatidylcholine (DSPC), dimyristoylphosphatidylcholine (DMPC) and dipalmitoylphosphatidylcholine (DPPC)], phosphatidylethanolamine, phosphatidylinositol, phosphatidylserine, phosphatidylglycerol, diphosphatidylglycerol, lysophosphatidylcholine and sphingomyelin.

The term "non-phospholipid-based surface active agent" means ionic and twitterionic surface active agents not containing a phosphate group as a functional group, examples of which may include 3-[(3-cholamidopropyl)dimethylamino]-2-hydroxy-1-propanesulfonate (CHAPSO), 3-[(3-cholamidopropyl)dimethylamino]-propanesulfonate (CHAP) and N,N-bis(3-D-gluconamidopropyl)-cholamide.

Next, water-solubilizing agents on the basis of the pseudomicelle type will be described. Water-soluble macromolecules to be used for this type are those having a weight average molecular weight of from 10,000 to 50,000,000 (preferably from 10,000 to 5,000,000). Weight average molecular weights here are based on values as determined by gel permeation high performance liquid chromatography using pullulan as the standard.

The above water-soluble macromolecules are not particularly limited as long as they have the above-specified molecular weights, examples of which may include compounds selected from various vegetable-based surface active agents, water-soluble polysaccharides, such as alginates, (for example, alginic acid, propylene glycol alginate), gum arabic, xanthan gum, hyaluronic acid, chondroitin sulfate, water-soluble celluloses, such as cellulose acetate, methyl cellulose, hydroxypropyl methyl cellulose, chitosan, chitin; water-soluble proteins, such as gelatin, collagen; polyoxyethylene-polyoxypropylene block copolymer; and DNA.

The water-solubilizing agents according to the present invention (the micelle and pseudo types) will then be described with respect to other requirement. First, the water-solubilizing agents according to the present invention are in the form of an aqueous solution during use. Nevertheless, any water-solubilizing agents which are brought into the form of an aqueous solution before use shall be included in the concept of "water-solubilizing agent", including not only aqueous solutions but also liquid concentrates, kits divided into parts and dry types which are brought into an aqueous solution before use.

For the micelle type, the content of a surface active agent must be equal to or higher than the critical concentration of the micelles forming microsomes when in the form of an aqueous solution. Usually, the content is from 0.2 to 10 mmol per liter of aqueous solution for 1 g of crude product. For the pseudomicelle type, the content of a water-soluble macromolecule is not particularly limited. Usually, the content is from 5 to 50 g per liter of aqueous solution for 1 g of crude product.

It is preferable that the water-solubilizing agent according to the present invention further comprises a nanocarbon-permeating substance and an oxidizing agent and is in the form of an aqueous alkaline solution. This preferred embodiment will then be described below.

First, the term "nanocarbon-permeating substance" means a substance having a diameter which is smaller than the C—C lattice size of a nanocarbon. A nanocarbon-permeating cation having such a diameter (ion diameter), specifically a lithium ion may be mentioned for example. A hydrogen ion is smaller than the lattice size, but is lost in water in the form of an oxonium ion and is therefore unsuitable as a nanocarbon-permeating cation. The role of such a nanocarbon-permeating substance is not revealed as of now. It is however assumed that it is responsible for altering the charge state within the nanocarbon and displacing impurities on the surface of the interior of the nanocarbon and inside the nanocarbon by pervading through the nanocarbon.

The content of the nanocarbon-permeating substance is preferably from 0.1 to 1 mol per liter of aqueous solution for 1 g of crude nanocarbon product.

Next, oxidizing agents will be described. Usable oxidizing agents are not particularly limited. Nevertheless, persulfates (persulfate ions in solution) are preferable because persulfates are alkaline and highly active and converted to sulfuric acid after being oxidized, which makes them easy to be aftertreated.

Description will then be made on the pH. It is preferable that the pH ranges from 6 to 14 (preferably alkaline). Reasons for suitability of a liquid being in this range is not clear. It is however assumed to be responsible for altering the electronic state on the surface of the nanocarbon and, for a nanocarbon tube, for softening the surface of the carbon and folding the carbon nanotube. Preferably, the pH ranges from 10 to 14 for the micelle type and from 6 to 12 for the pseudomicelle type.

Description will then be made on the process for using the water-solubilizing agent according to the invention for refining nanocarbons (that is, a process for refining nanocarbons according to the present invention). The process for producing high-purity nanocarbons according to the present invention will not be described because the step of solubilizing, one of the steps thereof, is per se the process for refining to be described below and the other steps of producing crude nanocarbons, etc. are well known at the time of filing of this application (as illustrated below).

Crude products which may be refined according to this refining process are not particularly limited. The process may effectively be applied to any crude products as obtained by any of the syntheses including electrical discharge (C. Journet et al., Nature 388, 756 (1997) and D. S. Bethune et al., Nature 363, 605 (1993)), laser vapor deposition (R. E. Smalley et al., Science 273, 483 (1996)), gaseous synthesis (R. Andrews et al., Chem. Phys. Lett., 303, 468, 1999), thermochemical gaseous vapor deposition (W. Z. Li et al., Science, 274, 1701 (1996), Shinohara et al., Jpn. J. Appl. Phys. 37, 1257 (1998), plasma chemical gaseous vapor deposition (Z. F. Ren et al., Science. 282, 1105 (1998)).

It is preferable to treat a crude product with an acid when a metal catalyst has been used for its synthesis in order to remove the metal catalyst before adding the crude product to the water-solubilizing agent according to the invention (aqueous solution for refining). For acid treatment, a procedure as described in Japanese Unexamined Patent Publication No. 2001-26410 may be mentioned, in which a solution of nitric acid or hydrochloric acid is used as an acid solution, being diluted fifty-fold with water in either case. After such acid treatment, the crude product is washed with water and filtered for subsequent dissolution.

Then the crude product containing nanocarbons (for example, carbon nanotubes) is introduced to the solubilizing agent (aqueous solution for refining) according to the invention. Amounts to be introduced are not particularly limited. Nevertheless, 1 to 5 g of the crude product for the micelle type or 1 to 10 g of the crude product for the pseudomicelle type are usually introduced per liter of the aqueous solution for refining.

After introduction, the crude product is preferably ultrasonicated first for about five minutes for the micelle type in order to completely dissolve the nanocarbons (carbon nanotubes, for example). It is then completely dissolved in six hours at a room temperature or in several minutes with heating at 60° C.

For the pseudomicelle type, a mixture containing a pseudomicelle-forming substance (sodium alginate, for example), a permeator (lithium hydroxide, for example), an oxidizing agent (sodium persulfate, for example), nanocarbons and deionized water is thoroughly diffused and dispersed by a homogenizer, before leaving it at rest at 40° C. for about one day. When no permeators or oxidizing agents are used, it is left at rest at 40° C. for about one week.

After being completely dissolved, the nanocarbons (carbon nanotubes, for example) are removed from the solution by any conventional means. For the micelle types, for example, the nanocarbon (for example, carbon nanotube) solution is subjected to chromatography and fractionated according to sizes and water is added to the fraction of nanocarbons (carbon nanotubes, for example) to bring it below the critical micelle concentration so that nanocarbons (carbon nanotubes, for example) may be removed.

In addition, for the pseudomicelle type, when sodium alginate is used as a micelle-forming substance for example, 90% formic acid is used to selectively hydrolyze alginic acid so that refined nanocarbons may be removed by filtration.

Thus, according to the invention, various impurities, for example, unwanted carbonaceous impurities such as graphite and transition metals, which may be produced depending on the processes for synthesizing nanocarbons can economically and effectively be eliminated, with a result that high-purity nanocarbons may be obtained.

EXAMPLES

The present invention will specifically be demonstrated using Examples below. The present invention is not to be limited to Examples.

Preparation of Aqueous Solution for Refining Carbon Nanotubes

Aqueous solutions for refining carbon nanotubes were prepared according to the formulations in Table 1 below. The diameters of microsomes in the solutions were measured by ELS-8000 available from Otsuka Electronics Co. Ltd.

TABLE 1

|  | Ex. 1 | Ex. 2 | Ex. 3 | Ex. 4 | Ex. 5 | Ex. 6 |
|---|---|---|---|---|---|---|
| included microsome (mM) | DSPC 0.3 | DMPC 0.3 | DPPC 0.3 | CHAPSO 5.0 | CHAPS 5.0 | Big-CHAP 5.0 |
| LiOH (M) | 0.1 | 0.1 | 0.1 | 0.1 | 0.1 | 0.1 |
| $(NH_4)_2S_2O_8$ (M) | 0.05 | 0.05 | 0.05 | 0.05 | 0.05 | 0.05 |
| diameter of microsome (nm) | 100 | 200 | 300 | 56 | 51 | 76 |
| pH of aqueous solution | 12 | 12 | 12 | 12 | 12 | 12 |

Example 1

Decatalyzation

One gram of CVD crude single-layered carbon nanotubes (purity: approximately 30%) was first decatalyzed with 1000 ml of mixed solution of hydrochloric acid and nitric acid (0.1 M and 0.1 M) at 60° C. for 30 minutes, and was then neutralized with 5 N NaOH solution and dried in a temperature-controlled bath (85° C.) for three hours.

Refining

The carbon nanotubes obtained from the above decatalyzation were added to one liter of aqueous solution for refining carbon nanotubes and ultrasonicated for about 10 minutes. This blend of the carbon nanotubes and the aqueous solution for refining carbon nanotubes was then warmed from the room temperature to 60° C. in a hot water bath and left for about 10 minutes to completely dissolve the carbon nanotubes in the aqueous solution.

Recovery

A large amount of water was introduced to the carbon nanotube solution obtained from the above refining to bring the solution below the critical micelle concentration to obtain deposited carbon nanotubes. Recovery of the carbon nanotubes was determined to be 99.5%.

Examples 2 to 6

In a similar manner to Example 1, recovery of carbon nanotubes was determined. The results are shown in Table 2.

TABLE 2

|  | Ex. 2 | Ex. 3 | Ex. 4 | Ex. 5 | Ex. 6 |
|---|---|---|---|---|---|
| Recovery (%) | 75.1 | 78.2 | 23.8 | 23.5 | 45.2 |

Example 7

A commercially available sodium alginate (Wako Pure Chemical Industries, Ltd., weight average molecular weight 500,000) and nanocarbons (weight ratio 4:1) were added to deionized water (1%, 5% and 2% in terms of the weight ratio of the sodium alginate to the deionized water). After thorough stirring, it was left at rest at 40° C. for about one week. Thereafter, the weight ratio of the sodium alginate, the nanocarbons and the deionized water was diluted to about 4:1:10000 to obtain a clear aqueous solution. Then, infrared spectrum, zeta potential measurement and a transmission electron microscope were used to observe the presence of a complex of sodium alginate and nanocarbons. Thereafter, 90% formic acid was added to this aqueous solution to selectively hydrolyze the sodium alginate and filtration was performed to obtain refined nanocarbons. The results are shown in Table 3.

TABLE 3

|  | Single-layered carbon nanotubes | multi-layered carbon nanotubes | carbon nanofibers |
|---|---|---|---|
| sodium alginate/ deionized water (weight ratio) | 1% | 5% | 2% |
| recovery (%) | 99.5 | 97.8 | 99.4 |

Example 8

Two grams of decatalyzed CVD crude single-layered carbon nanotubes (purity: approximately 30%) were added to 100 ml of an aqueous solution at pH 12.8 containing 0.2 M lithium hydroxide, 0.1 M ammonium persulfate and the above sodium alginate (20 mg/ml) and thoroughly mixed by a homogenizer, before leaving it at rest at 40° C. for about one day. Thereafter, insoluble impurities were removed by a centrifuge at 3000 G and the uniformly dispersed, ink-like mixed solution was treated with formic acid (90%) at 100° C. The refined single-layered carbon nanotubes were separated off by high-pressure filtration, thoroughly washed with deionized water and dried at 120° C. to obtain 0.42 g of high-purity single-layered carbon nanotubes.

The invention claimed is:

1. An aqueous nanocarbons solution comprising:
   nanocarbons, and
   an active ingredient which is a surface active agent which is one or more selected from the group consisting of distearoylphosphatidylcholine (DSPC), dimyristoylphosphatidylcholine (DMPC), dipalmitoylphosphatidylcholine (DPPC), 3-[(3-cholamidopropyl)dimethylamino]-2-hydroxy-1-propanesulfonate (CHAPSO), 3-[(3-cholamidopropyl)dimethylamino]-propanesulfonate (CHAP) and N,N-bis (3-D-gluconamidopropyl)-cholamide, and wherein the active ingredient encapsulates the nanocarbons in globular micelles or pseudo micelles.

2. The solution according to claim 1, which further comprises a nanocarbon-permeating substance and an oxidizing agent and the pH ranges from 6 to 14.

3. The solution according to claim 2, wherein the nanocarbon-permeating substance is lithium ion.

4. The solution according to claim 2, wherein the oxidizing agent is a persulfate.

5. The solution according to claim 1, wherein the nanocarbons are carbon nanotubes (single- and multi-layered types and cup-stack types), carbon nanofibers or carbon nanohorns.

6. A process for producing an aqueous nanocarbons solution comprising the step of adding a crude product to an aqueous solution containing as an active ingredient to encapsulate the nanocarbon in the crude product, a surface active agent selected from the group consisting of distearoylphosphatidylcholine (DSPC), dimyristoylphosphatidylcholine (DMPC), dipalmitoylphosphatidylcholine (DPPC), 3-[(3-cholamidopropyl)dimethylamino]-2-hydroxy-1-propanesulfonate (CHAPSO), 3-[(3-cholamidopropyl)dimethylamino]-propanesulfonate (CHAP) and N,N-bis (3-D-gluconamidopropyl)-cholamide, and wherein the active ingredient encapsulates the nanocarbons in globular micelles or pseudo micelles.

\* \* \* \* \*